United States Patent
Waddington et al.

(10) Patent No.: US 12,005,029 B2
(45) Date of Patent: *Jun. 11, 2024

(54) DENSITY FLOW METER FOR PHARMACEUTICAL FORMULATION DOSING

(71) Applicant: Catalent U.K. Swindon Zydis Limited, Swindon (GB)

(72) Inventors: David Waddington, Swindon (GB); Matthew Wort, Lyneham (GB); Katherine Arneil, Faringdon (GB)

(73) Assignee: Catalent U.K. Swindon Zydis Limited, Swindon (GB)

(*) Notice: Subject to any disclaimer, the term of this patent is extended or adjusted under 35 U.S.C. 154(b) by 307 days.

This patent is subject to a terminal disclaimer.

(21) Appl. No.: 17/529,731

(22) Filed: Nov. 18, 2021

(65) Prior Publication Data

US 2022/0071847 A1 Mar. 10, 2022

Related U.S. Application Data

(63) Continuation of application No. 16/943,853, filed on Jul. 30, 2020, now Pat. No. 11,185,470.

(Continued)

(51) Int. Cl.
*A61J 1/20* (2006.01)
*A61J 1/03* (2023.01)
(Continued)

(52) U.S. Cl.
CPC .............. *A61J 1/20* (2013.01); *B65B 3/003* (2013.01); *B65B 3/12* (2013.01); *G01F 1/84* (2013.01);
(Continued)

(58) Field of Classification Search
CPC .. A61J 1/20; A61J 1/035; B65B 3/003; B65B 3/12; G01F 1/84; G01N 9/002; A61K 47/20
(Continued)

(56) References Cited

U.S. PATENT DOCUMENTS 4,159,248 A * 6/1979 Taylor .................... B01D 21/00
210/195.3
5,156,194 A 10/1992 Von et al.
(Continued)

FOREIGN PATENT DOCUMENTS

CN 1500203 A 5/2004
CN 107708768 A 2/2018
(Continued)

OTHER PUBLICATIONS

International Search Report and Written Opinion mailed Oct. 23, 2020, directed to International Application No. PCT/EP2020/071428; 15 pages.
(Continued)

*Primary Examiner* — Bob Zadeh
*Assistant Examiner* — Michael J. Melaragno
(74) *Attorney, Agent, or Firm* — Morrison & Foerster LLP

(57) ABSTRACT

Provided are systems and method for dosing a pharmaceutical formulation. These methods and systems can displace the pharmaceutical formulation through a density flow meter, wherein the density flow meter is configured to measure a density of the pharmaceutical formulation. Next, the pharmaceutical formulation can be dosed into preformed molds and the dosing process can be stopped when the density of the pharmaceutical formulation measured by the density flow meter is below a predetermined threshold.

15 Claims, 3 Drawing Sheets

Related U.S. Application Data

(60) Provisional application No. 62/881,145, filed on Jul. 31, 2019.

(51) Int. Cl.
    *A61K 47/20*     (2006.01)
    *B65B 3/00*     (2006.01)
    *B65B 3/12*     (2006.01)
    *G01F 1/84*     (2006.01)
    *G01N 9/00*     (2006.01)

(52) U.S. Cl.
    CPC ............... *G01N 9/002* (2013.01); *A61J 1/035* (2013.01); *A61K 47/20* (2013.01)

(58) Field of Classification Search
    USPC .......................................................... 222/1
    See application file for complete search history.

(56) References Cited

U.S. PATENT DOCUMENTS

| | | | |
|---|---|---|---|
| 5,168,905 A | 12/1992 | Phallen | |
| 5,996,650 A | 12/1999 | Phallen et al. | |
| 7,908,097 B2 * | 3/2011 | Duffill | G01F 1/8477 702/45 |
| 2002/0100505 A1 | 8/2002 | Keilty et al. | |
| 2003/0154804 A1 | 8/2003 | Henry et al. | |
| 2005/0270899 A1 | 12/2005 | Phallen et al. | |
| 2006/0051347 A1 * | 3/2006 | Winter | C07K 1/34 530/387.3 |
| 2016/0279246 A1 * | 9/2016 | Trout | A61K 31/167 |
| 2018/0028750 A1 | 2/2018 | Dahlin et al. | |
| 2019/0063182 A1 | 2/2019 | Fripp et al. | |
| 2019/0084706 A1 | 3/2019 | Heaggans et al. | |
| 2019/0276707 A1 | 9/2019 | Wong et al. | |
| 2021/0030623 A1 | 2/2021 | Waddington et al. | |

FOREIGN PATENT DOCUMENTS

| | | |
|---|---|---|
| EP | 2624815 B1 | 8/2016 |
| JP | H6-503055 A | 4/1994 |
| JP | 2003-528306 A | 9/2003 |
| JP | 2013-123702 A | 6/2013 |
| JP | 2019-505451 A | 2/2019 |

OTHER PUBLICATIONS

Allowance of Patent dated Mar. 29, 2022, directed to KR Application No. 102022-7001485; 3 pages.

Examination Report dated Jan. 11, 2002, directed to AU Application No. 2020323703; 2 pages.

Office Action dated Dec. 14, 2022, directed to PH Application No. 1-2021-553189; 5 pages.

First Office Action dated Sep. 29, 2022, directed to CN Application No. 202080054349.7; 18 pages.

Notification of Reasons for Rejection dated Aug. 3, 2022, directed to JP Application No. 2022-506226; 6 pages.

Office Action dated Aug. 30, 2022, directed to RU Application No. 2022104395; 13 pages.

Decision on Rejection dated Apr. 12, 2023, directed to CN Application No. 202080054349.7; 11 pages.

* cited by examiner

DENSITY FLOW METER FOR PHARMACEUTICAL FORMULATION DOSING

CROSS-REFERENCE TO RELATED APPLICATIONS

This application is a continuation of U.S. application Ser. No. 16/943,853, filed Jul. 30, 2020, which claims the benefit of U.S. Provisional Application No. 62/881,145, filed Jul. 31, 2019, the entire contents of which are incorporated herein by reference.

FIELD

This disclosure relates to systems and methods for reducing risk of air ingress into dosed pharmaceutical formulations. More specifically, this disclosure relates to systems and methods that employ a density flow meter to reduce the risk of air ingress into dosed pharmaceutical formulations.

BACKGROUND

In a typical procedure for forming pharmaceutical dosage forms, a pharmaceutical formulation (i.e., suspension or solution) is drawn from a storage vessel and aliquots of such formulations are deposited into preformed blister packs/molds. When the level of the pharmaceutical formulation reaches the bottom of the storage vessel, the batch is done and the dosing process should be stopped in order to prevent air ingress into the final units dosed. This end point for each batch is normally visually assessed by an operator. If the operator misses this end point, air can be drawn into the storage vessel's recirculation system by a recirculation pump and the aerated formulation is then dosed into the preformed blister packs/molds. Air ingress in the final dosage forms can result in under-weight or under-potent dosage units. In some instances, the operator may determine the end point too early resulting in lost product and therefore low yield. The operator's determination of the end point can create variability in the dosing process and thus a potential lower assurance of overall product quality at the end of dosing.

There are many reasons as to why the operator may not be able to accurately visually assess the end point for each batch. For example, it can often be difficult for the operator to see the bottom of the storage vessel due to their size. In addition, some storage vessels are designed with a small sight glass for an operator to see into the storage vessel. Furthermore, the sight glass can be covered in condensation and/or the view of the storage vessel's bottom is constantly interrupted by the stirring mechanism within the storage vessel. As such, these issues can combine to obstruct the operator's visual determination of the batch end point leading to a higher risk of air ingress during the dosing process.

SUMMARY

Applicants have discovered systems and methods that employ a density flow meter to reduce the risk of air ingress when dosing pharmaceutical formulations susceptible to foaming. As explained in the background section, a conventional dosing process requires visual assessment of the mix level in the pharmaceutical storage vessel as well as the assessment of the end point for the dosing process. This can result in the end point being missed resulting in air ingress into the final dosage forms or the end point being determined too early resulting in reduced product yield.

Various other solutions were identified as possible fixes for the problems addressed in the background section including formulation changes (however, its normally too late in the development process to change the formulation), optimization of holding conditions in the storage vessel (stirrer speeds, temperatures are all assessed during development; however, sometimes the stirrer speeds need to be kept at a speed that might promote a level of foaming in order to keep the suspension homogenous), use of different storage vessels (one that may make it easier for the operator to assess the amount of formulation remaining; however, this still does not remove the manual input/operator perception part of the problem). Applicants determined that the best solution to the problems is a system that utilizes a density flow meter to prevent air ingress into the dosed pharmaceutical product by automatically stopping dosing when the density of the pharmaceutical formulation from the storage vessel falls below a certain level. As such, the use of a density flow meter during the dosing process can eliminate operator visual determination of the end point for a batch.

The typical use for a density flow meter is to monitor in-process density of a fluid traveling through a tube by way of measuring the Coriolis Effect. This in-process measurement is typically used to control the mass flow of the fluid. Another typical use for a density flow meter is to support concentration measurements of a fluid (amount of solute contained per unit volume). In contrast to these typical in-process uses, the density flow meter in Applicants' systems can be used to control the uniformity of the end product.

In some embodiments, a system for dosing a pharmaceutical formulation includes a vessel for storing a pharmaceutical formulation; a recirculation system comprising a density flow meter fluidly connected to the vessel and a recirculation pump fluidly connected to the density flow meter and the vessel, wherein the recirculation pump is configured to displace the pharmaceutical formulation from the vessel through the density flow meter and the density flow meter is configured to measure a density of the pharmaceutical formulation; at least one pump fluidly connected to the recirculation system, wherein the at least one pump is configured to displace the pharmaceutical formulation from the recirculation system and into preformed molds, wherein the at least one pump is configured to stop displacing the pharmaceutical formulation from the recirculation system when the density of the pharmaceutical formulation measured by the density flow meter is below a predetermined threshold. In some embodiments, the system comprises a computer, wherein the computer, the density flow meter, and the at least one pump are communicatively coupled with one another. In some embodiments, the density flow meter is configured to send data comprising the density of the pharmaceutical formulation to the computer. In some embodiments, the computer is configured to send one or more instruction or control signals to the at least one pump to alter an activation state of the pump. In some embodiments, the activation state comprises an on configuration and an off configuration. In some embodiments, the one or more instruction or control signals sent from the computer to the at least one pump comprises a signal to turn the at least one pump off when the data comprising the density of the pharmaceutical formulation is below a predetermined threshold. In some embodiments, the computer, the density flow meter, and the at least one pump are wirelessly communicatively coupled with one another. In some embodiments, the recirculation pump is configured to displace the pharmaceutical formulation from the vessel through the density flow meter, through the recirculation pump, and back into the vessel. In some embodiments, the recirculation system further comprises a manifold. In some embodiments, the recirculation pump is configured to displace the pharmaceutical formulation from the vessel through the density flow meter, through the recirculation pump, through the manifold, and back into the vessel. In some embodiments, the at least one pump is configured to displace the pharmaceutical formulation from the manifold and into preformed molds. In some embodiments, the vessel comprises a stirrer. In some embodiments, the pharmaceutical formulation comprises at least one surfactant such as sodium lauryl sulfate and sodium docusate.

In some embodiments, a method for dosing a pharmaceutical formulation includes storing a pharmaceutical formulation in a vessel; displacing the pharmaceutical formulation from the vessel through a density flow meter, wherein the density flow meter is configured to measure a density of the pharmaceutical formulation; dosing the pharmaceutical formulation into preformed blister packs/molds; stopping the dosing of the pharmaceutical formulation into preformed blister packs/molds when the density of the pharmaceutical formulation measured by the density flow meter is below a predetermined threshold. In some embodiments, the density flow meter is configured to send data comprising the density of the pharmaceutical formulation to a computer. In some embodiments, the computer is configured to send one or more instruction or controls signals to stop the dosing of the pharmaceutical formulation when the data comprising the density of the pharmaceutical formulation is below a predetermined threshold. In some embodiments, the computer sends the one or more instruction or control signals to stop dosing of the pharmaceutical formulation to at least one pump. In some embodiments, the computer, the density flow meter, and the at least one pump are wirelessly communicatively coupled with one another. In some embodiments, the method includes recirculating a portion of the pharmaceutical formulation to the vessel after passing through the density flow meter. In some embodiments, the pharmaceutical formulation comprises at least one surfactant such as sodium lauryl sulfate and sodium docusate.

Additional advantages will be readily apparent to those skilled in the art from the following detailed description. The examples and descriptions herein are to be regarded as illustrative in nature and not restrictive.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

BRIEF DESCRIPTION OF THE DRAWINGS

The invention will now be described, by way of example only, with reference to the accompanying drawings, in which.

DETAILED DESCRIPTION

Figure 1:
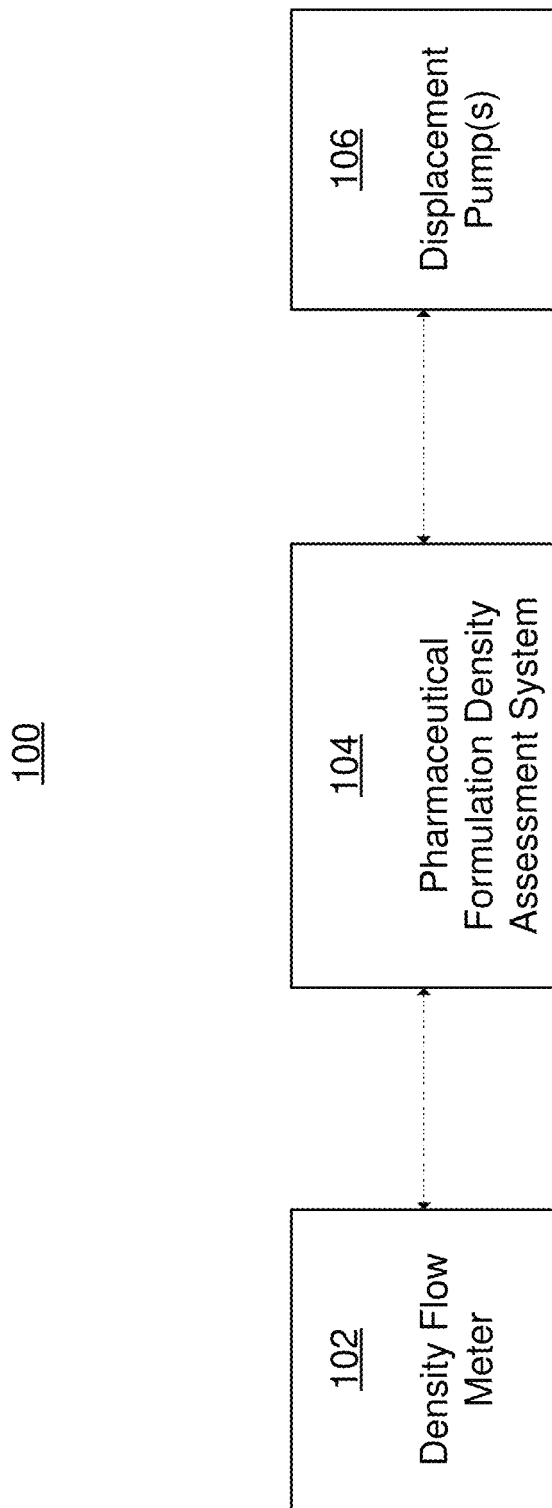
FIG. 1 illustrates a system for reducing air ingress during pharmaceutical formulation dosing according to some embodiments.

Applicants have discovered systems and methods that employ a density flow meter to reduce the risk of air ingress when dosing pharmaceutical formulations. Specifically, Applicants' system utilizes a density flow meter to prevent air ingress into the dosed pharmaceutical product by automatically stopping dosing when the density of the pharmaceutical formulation from the storage vessel falls below a certain level. As such, the use of a density flow meter during the dosing process can eliminate operator visual determination of the end point for a batch.

The systems and methods disclosed herein are capable of measuring the density of the pharmaceutical formulation that is used to produce a dosage form. The pharmaceutical formulation can include a variety of components including at least a matrix former, a structure former, a solvent, an API, and/or other pharmaceutically acceptable agents or excipients. The matrix former can provide the network structure of the dosage form that imparts strength and resilience during handling. Suitable matrix formers can include, without limitation, gelatin, pullulan, starch, or combinations thereof. Additional matrix formers can be found in EP 2624815 B1, which is herein incorporated by reference in its entirety. The gelatin can be fish gelatin, bovine gelatin, porcine gelatin, or combination thereof. Each of the gelatins can have different gelling characteristics. The extent a gelatin solution forms a gel can be dependent on the concentration of the gelatin and the temperature of the gelatin solution. A solution of bovine gelatin tends to gel at temperatures of less than 18° C. and thus can be considered a gelling gelatin. In contrast, fish gelatin can remain in solution at temperatures as low as 5° C. and thus can be considered a non-gelling gelatin. In some embodiments, the gelatin can be a low endotoxin gelatin such as one sourced or one produced according to the process disclosed in Provisional Application No. 62/640,394, which is hereby incorporated by reference in its entirety. In some embodiments, the fish gelatin can be high molecular weight fish gelatin, standard molecular weight fish gelatin, or combinations thereof. High molecular weight fish gelatin is defined as a fish gelatin in which more than 50% of the molecular weight distribution is greater than 30,000 Daltons. Standard molecular weight fish gelatin is defined as fish gelatin in which more than 50% of the molecular weight distribution is below 30,000 Daltons.

Suitable structure formers for the pharmaceutical formulation can include sugars including, but not limited to, mannitol, dextrose, lactose, galactose, cyclodextrin, or combinations thereof. The structure former can be used in freeze drying as a bulking agent as it crystalizes to provide structural robustness to the freeze-dried product. The solvent in the pharmaceutical formulation can be water (e.g., purified water).

The pharmaceutical formulation will include at least one active pharmaceutical ingredient. The active ingredient may be an active pharmaceutical ingredient, biologic or vaccine antigen for the treatment of human or veterinary diseases. The active ingredient is the component that the dosage form is used to deliver. Active ingredients may be one or more of antibacterial agents, antifungal agents, antiprotozoal agents, antiviral agents, labor-inducing agents, spermicidal agents, prostaglandins, steroids and microbicides, proteins/peptides and vaccine antigens. The active pharmaceutical ingredient may be a single active pharmaceutical ingredient, such as a single chemical entity, or it may be a mixture of several active pharmaceutical ingredients. The active pharmaceutical ingredient may be of any of the many categories of active pharmaceutical ingredients. The active pharmaceutical ingredient may be selected from, but is not limited to, the group consisting of acyclovir, fluconazole, progesterone and derivatives thereof, nonoxylenol-9, terbutaline, lidocaine, testosterone and derivatives, dinoprostone, lactobacillus, estrogen and derivatives, naphthalene2-sulfonate, butoconazole, clindamycin nitrate/phosphate, neomycine sulfate, polymyxin sulfate, nystatin, clotrimazole, dextrin sulphate, glyminox, miconazole nitrate, benzalkonium chloride, sodium lauryl sulphate, tenofovir, insulin, calcitonin, danazol, acriflavine, leuprorelin acetate, metronidazole, benzydamine hydrochloride, chloramphenicol, oxybutynin, ethinyl estradiol, prostaglandins, insulin, calcitonin and combinations thereof. The active pharmaceutical ingredient may also be vaccine antigen such as those for the treatment of Hepatitis B, HIV, HPV, Chlamydia, gonococcal infections.

Active ingredients may include salts, esters, hydrates, solvates and derivatives of any of the foregoing active ingredients. Suitable derivatives are those that are known to skilled persons to possess the same activity as the active ingredient though the activity level may be lower or higher.

Additional pharmaceutically acceptable agents or excipients for the pharmaceutical formulation include, without limitation, sugars, such as mannitol, dextrose, and lactose, inorganic salts, such as sodium chloride and aluminum silicates, gelatins of mammalian origin, fish gelatin, modified starches, preservatives, antioxidants, surfactants, chelating agents, viscosity enhancers, coloring agents, flavoring agents, pH modifiers, sweeteners, taste-masking agents, and combinations thereof. Suitable coloring agents can include red, black and yellow iron oxides and FD & C dyes such as FD & C Blue No. 2 and FD & C Red No. 40, and combinations thereof. Suitable flavoring agents can include mint, raspberry, licorice, orange, lemon, grapefruit, caramel, vanilla, cherry and grape flavors and combinations of these. Suitable pH modifiers can include citric acid, tartaric acid, phosphoric acid, hydrochloric acid, maleic acid, sodium hydroxide (e.g., 3% w/w sodium hydroxide solution), and combinations thereof. Suitable sweeteners can include, sucralose aspartame, acesulfame K and thaumatin, and combinations thereof. Suitable taste-masking agents can include a range of flavorings and combinations thereof.

In some embodiments, the pharmaceutical formulations containing excipients may create a head of foam on the mixture of the pharmaceutical formulation and/or may create foam throughout the mixture process of the pharmaceutical formulation. In addition, there are some excipients that can cause foaming when the formulation is agitated (e.g., hydroxypropyl methyl cellulose ("HPMC") and polyvinylpyrrolidone ("PVP")). The most common component of the pharmaceutical formulation that can cause foaming are surfactants and the amount of foaming can be dependent on the type of surfactant. Anionic surfactants such as sodium alkyl sulphates (e.g., sodium lauryl sulphate) can cause foaming. Although non-ionic surfactants such as sorbitan esters and polysorbates can foam less than anionic surfactants, the foams can be quite stable and difficult to remove. Cationic surfactants (e.g., quaternary ammonium and pyridinium cationic surfactants) can also foam, but these foams are less stable and easier to get rid of.

During the dosing process, a pharmaceutical formulation is dosed into a preformed mold. As used herein, "dosed" refers to the deposition of a pre-determined aliquot of solution or suspension. As used herein, "preformed mold" refers to any suitable container or compartment into which an aqueous solution or suspension may be deposited and within which subsequently freeze dried. In certain embodiments of the present disclosure, the preformed mold is a blister pack with one or more blister pockets. Predetermined aliquots in an amount of about 125-1500 mg or about 500 mg wet filling dosing weight of the pharmaceutical formulation can be metered into preformed molds. The minimum unit size (wet fill weight, 125 mg) can be selected to minimize the amount of active pharmaceutical ingredient ("API") in solution proportionally to the unit dose, and therefore its surface area and potential for oxidative degradation in the final dosage form.

Figure 2:
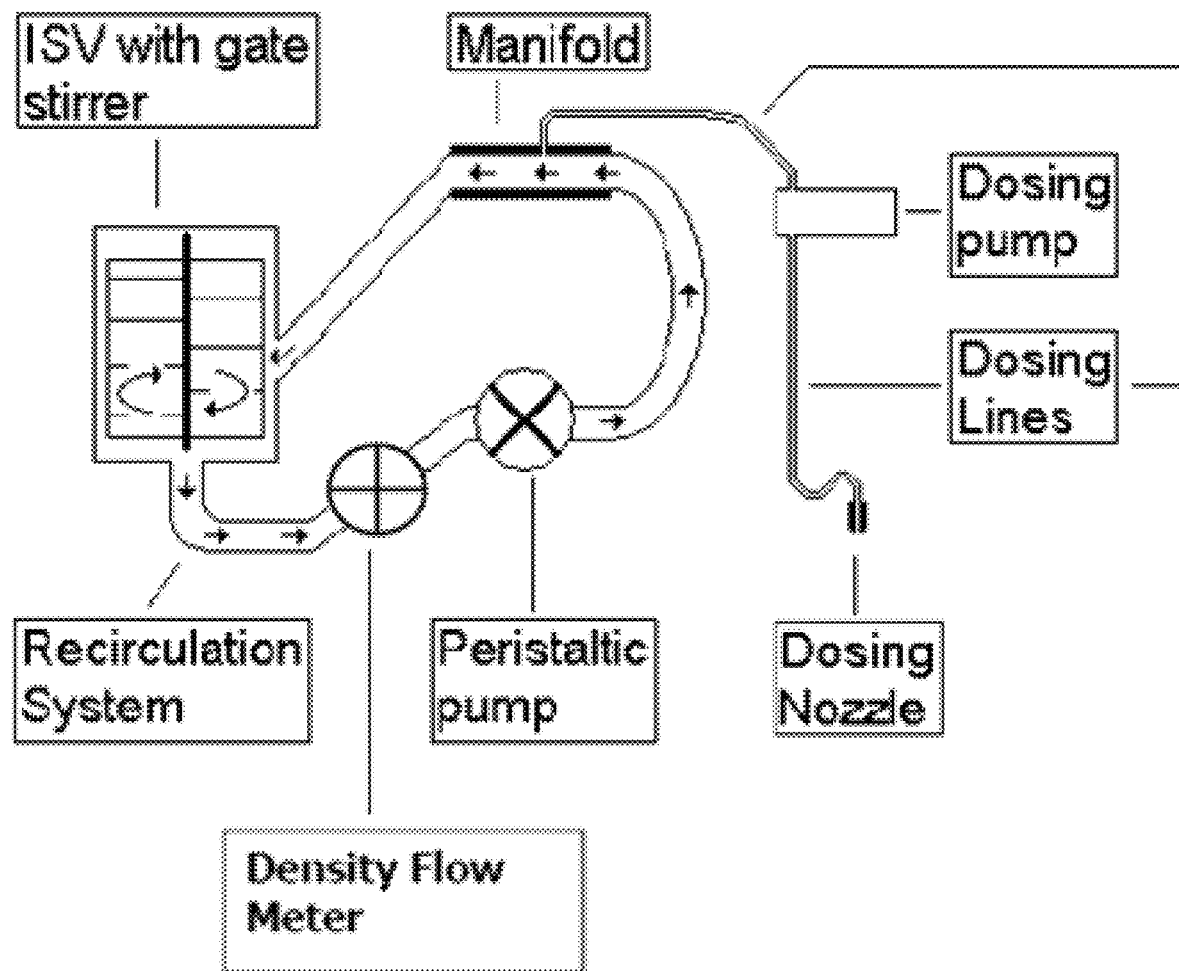
FIG. 2 illustrates a system for reducing air ingress during pharmaceutical formulation, in accordance with some embodiments.

Prior to dosing, the pharmaceutical formulation can be stored in a storage vessel. In some embodiments, the storage vessel can be an intermediate storage vessel. The storage vessel can have a stirrer to continuously mix the pharmaceutical formulation in the storage vessel. In some embodiments, the stirrer can be a gate stirrer as depicted in FIG. 2. In some embodiments, the storage vessel is not capable of de-aerating the pharmaceutical formulation if foam is present (i.e., if temperature and lower stirring speeds do not sort out the foam, then pulling vacuum is the only other option).

FIG. 2 illustrates a system for reducing air ingress during pharmaceutical formulation. As shown in FIG. 2, the storage vessel can be connected to a recirculation system. The recirculation system can include a recirculation pump fluidly connected to the storage vessel. The recirculation pump can circulate the pharmaceutical formulation through the recirculation system such that the formulation is continuously moving. The recirculation system can also include at least one manifold fluidly connected to the recirculation pump and the storage vessel. The at least one manifold can be used as a branching device for the pharmaceutical formulation to be split into several different dosing lines for deposition into the individual preformed molds. As such, the pharmaceutical formulation can flow from the storage vessel through the recirculation pump, through the manifold, and back into the storage vessel.

The recirculation system can also include a density flow meter as shown in FIG. 2. In some embodiments, the recirculation pump displaces the pharmaceutical formulation from the storage vessel through the density flow meter. In some embodiments, the recirculation pump can draw the pharmaceutical formulation from the storage vessel, through a density flow meter, and through the at least one manifold. In some embodiments, the density flow meter is fluidly connected between the storage vessel and the recirculation pump. In some embodiments, the density flow meter is fluidly connected between the storage vessel and the manifold. In some embodiments, the recirculation pump can draw the pharmaceutical formulation from the storage vessel, through the density flow meter, through the recirculation pump, through a manifold(s), and into the storage vessel.

If the level of formulation in the storage vessel is too low, air can be drawn into the storage vessel's recirculation system by the recirculation pump. This air can then later be dosed into the preformed blister packs/molds with the pharmaceutical formulation, thereby resulting in underweight and/or under potent dosage forms. In some embodiments, the recirculation pump is a peristaltic pump.

In the conventional dosing process, an operator monitors the level of the pharmaceutical formulation in the storage vessel. Once the pharmaceutical formulation level has dropped below the level of the formulation return port (a port within the storage vessel used to determine the level of formulation remaining in the vessel to be dosed), the level is monitored more closely by the operator. As the level of the pharmaceutical formulation reaches a certain point in the vessel (e.g., the level of an inner well of the vessel or the base of a thermocouple housing of the vessel or the level of the formulation return port itself), the operator can obtain the end of batch dose weights and the dosing process can be stopped for that batch. Any remaining pharmaceutical formulation in the vessel after dosing has ended can be discarded.

As explained above, there are a variety of issues that can cause the operator to either miss the end of batch point or to end the batch too early. For example, the pharmaceutical formulation can include an API (e.g., Riluzole) that creates aeration and/or foam when in solution, thereby obscuring the end of the dosing batch by obstructing the operator's view of the bottom of the storage vessel. The API is not limited to Riluzole. For example, if a pharmaceutical formulation contains at least an API and a surfactant like SLS, the surfactant can reduce the surface tension of the formulation causing it prone to entrap air bubbles when the formulation is agitated resulting in foam. In addition, the pharmaceutical may include an excipient (e.g., docusate sodium) that creates aeration and/or foam, thereby obscuring the end of the dosing batch by obstructing the operator's view of the bottom of the storage vessel. For example, the pharmaceutical formulation may include sodium lauryl sulfate ("SLS") and/or sodium docusate which can create excessive foam build up during the dosing process. Furthermore, the process set points required to maintain the pharmaceutical formulation's homogeneity may create aeration and/or foam towards the end of the batch.

FIG. 1 depicts a system 100 for reducing air ingress during a pharmaceutical formulation dosing process according to some embodiments. As shown in FIG. 1, system 100 may include a density flow meter 102, pharmaceutical formulation density assessment system 104, and at least one displacement pump 106. Each of these components may be communicatively coupled with one another such that they may send and receive electronic information via network communication amongst one another. As shown in the example of FIG. 1, assessment system 104 may be communicatively coupled to both density flow meter 102 and to at least one displacement pump 106. In addition, the density flow meter can be fluidly connected to the storage vessel. As such, when the pharmaceutical formulation is drawn out of the storage vessel, it can flow through the density flow meter where its density can be measured. In some embodiments, the density flow meter can be part of the recirculation system as shown in FIG. 2. For example, the density flow meter can be fluidly connected between the storage vessel and the recirculation pump.

In some embodiments, density flow meter 102 can be used to provide a consistent and scientific end point to dosing and to prevent air ingress into the final dosage forms. In some embodiments, the density flow meter can measure the density of a fluid by way of measuring the Coriolis Effect. In some embodiments, the density flow meter is a Coriolis single tube mass flow meter. As such, when the pharmaceutical formulation is drawn out of the storage vessel, the density of the formulation can be measured by an evaluation of the frequency of vibration and temperature of the formulation. In some embodiments, the density flow meter is a density flow meter manufactured by Khrone. In some embodiments, the density flow meter measures density in $kg/m^3$. In some embodiments, the density flow meter can measure/monitor mass flow and density of the pharmaceutical formulation.

In some embodiments, the pharmaceutical formulation can be drawn out of the storage vessel by at least one displacement pump. In some embodiments, the pharmaceutical formulation can be drawn out of the recirculation system by at least one displacement pump labeled as dosing pump in FIG. 2. In some embodiments, the pharmaceutical formulation can be drawn out of the storage vessel by a plurality of displacement pumps. In some embodiments, the pharmaceutical formulation can be drawn out of the recirculation system by a plurality of displacement pumps. In some embodiments, the at least one displacement pump can be fluidly connected to the storage vessel, the density flow meter, the recirculation system, the at least one manifold, and/or the preformed blister packs/molds. The at least one displacement pump can be responsible for displacing the pharmaceutical formulation from the storage vessel to the preformed blister packs/molds. For example, the at least one displacement pump can displace the pharmaceutical formulation that is circulating in the recirculation system from the recirculation system to the preformed blister packs/molds. As shown in FIG. 2, the at least one displacement pump can displace the pharmaceutical formulation that is traveling through the at least one manifold of the recirculation system and cause the pharmaceutical formulation to flow through the dosing lines and out the dosing nozzle(s) into the preformed blister/molds. As such, the pharmaceutical formulation may transport though various tubes (i.e., dosing lines/tubes), the density flow meter, the recirculation pump, manifold(s), and the at least one displacement pump itself prior to being deposited in the preformed molds. As explained above, the manifold(s) can be used as a branching device for the pharmaceutical formulation to be split into several different dosing tubes for deposition into the individual preformed blister packs/molds.

In some embodiments, the at least one displacement pump displaces the pharmaceutical formulation from the recirculation system and into the preformed blister packs/molds. In some embodiments, the at least one displacement pump displaces the pharmaceutical formulation from the manifold(s) of the recirculation system and into the preformed blister packs/molds. In some embodiments, the at least one displacement pump displaces the pharmaceutical formulation from the storage vessel through the density flow meter. In some embodiments, the at least displacement pump can draw the pharmaceutical formulation from the storage vessel, through a density flow meter, and into preformed blister packs/molds. In some embodiments, the density flow meter is fluidly connected between the storage vessel and the at least one displacement pump. In some embodiments, the density flow meter is fluidly connected between the storage vessel and the manifold(s). In some embodiments, the at least one displacement pump can draw the pharmaceutical formulation from the recirculation system, through the at least one displacement pump (and dosing tubes/lines before and after the at least one displacement pump), and into preformed blister packs/molds (by way of the dosing nozzle(s)). In some embodiments, the at least one displacement pump can draw the pharmaceutical formulation from the manifold(s) of the recirculation system, through the at least one displacement pump (and dosing tubes/lines before and after the at least one displacement pump), and into preformed blister packs/molds (by way of the dosing nozzle(s)).

In some embodiments, pharmaceutical formulation density assessment system 104 can be any device or system comprising one or more computer processors configured to receive density data for the pharmaceutical formulation, assess and/or process the received density data, and to generate and transmit one or more output signals in accordance with the results of the density assessment. In some embodiments, assessment system 104 may be provided, in whole or in part, as all or part of a desktop computing device, laptop, tablet, mobile electronic device, dedicated density processing device, computing module processor, server, cloud computing system, distributed computing system, or the like. In some embodiments, pharmaceutical formulation density assessment system 104 may be provided locally with respect to displacement pump(s) 106 and/or density flow meter 104 (e.g., in the room where dosing occurs), while in some embodiments density assessment system 104 may be provided remotely from displacement pump(s) 106 and/or density flow meter 104 (e.g., outside the room where dosing occurs, at a remote server location, etc).

In some embodiments, assessment system 104 may be configured to receive density data from density flow meter 102 and to process the density data to determine whether the density of the pharmaceutical formulation is at or below a predetermined threshold in order to stop the dosing process. In some embodiments, the predetermined density threshold for a given pharmaceutical formulation can be input into the assessment system by an operator. For example, for a given pharmaceutical formulation, the acceptable densities for the formulation can be determined prior to the dosing process by studies performed prior to commercial dosing. These studies include review of data obtained throughout the dosing process to decipher the exact point at which density drops in relation to progress of dosing. This data is then used to set a limit whereby the density flow meter is programmed to cease dosing operations if the density drops below this limit. The operator can then input the density threshold into the assessment system prior to starting the dosing process. In some embodiments, the end point (i.e., the predetermined threshold density) is set during development studies and can typically be 50 kg/m$^3$ lower than the level recorded during the dosing process.

In some embodiments, assessment system 104 may be configured to send one or more instruction or control signals to displacement pump(s) 106 configured to cause displacement pump(s) to alter an activation state of the pump(s) (e.g., to turn from off to on, or turn from on to off); in some embodiments, as discussed in detail herein, the instruction or control signal may be sent by assessment system 104 in accordance with the determined density based on analysis of the density data received from density flow meter 102. For example, in some embodiments, if the density of the pharmaceutical formulation falls below a predetermined threshold, then a signal may be sent directing displacement pump(s) 106 to be turned off, thereby stopping the dosing process. In some embodiments, when displacement pump(s) 106 is turned off, no more pharmaceutical formulation will be drawn from the recirculation system. In some embodiments, when the density flow meter detects a change in the mass flow of the matrix (i.e., air ingress or particulate matter), an alarm can be triggered and the dosing procedure is automatically stopped.

As described herein, displacement pump(s) 106 may be configured to be turned off (i.e., stop displacing the pharmaceutical formulation from the recirculation system or storage vessel to the preformed molds) when the density of the pharmaceutical formulation measured by the density flow meter falls below a predetermined threshold. As discussed above, in some embodiments, displacement pump(s) 106 may be configured to have an activation state modified in accordance with an instruction signal or control signal received from pharmaceutical formulation density assessment system 104 by any wired or wireless electronic communication medium, including by any suitable network communication protocol.

Accordingly, when air begins to be drawn into the recirculation system for the storage vessel (i.e., when the storage vessel empties), the density of the pharmaceutical formulation can start to decrease with the addition of air to the formulation. This change can cause the density flow meter to signal to cease dosing. As such, the operator no longer is required to visually monitor the pharmaceutical formulation in the storage vessel. Instead, as the formulation's density reaches a predetermined threshold, the dosing process can stop. End of batch does weights can be taken and the batch can be automatically stopped. Thus, air ingress into the dosage forms can be prevented by this automatic ceasing of the dosing process when the density of the pharmaceutical formulation falls below a certain level.

After dosing, the dosed pharmaceutical formulations can be frozen in the preformed blister packs/molds. The dosed formulations in the preformed blister packs/molds can be frozen by any means known in the art. For example, the formulations can be passed through a cryogenic chamber (e.g., liquid nitrogen tunnel). In some embodiments, the frozen units in the preformed blister packs/molds can be collected and placed in a freezer prior to freeze drying. The frozen units can be freeze-dried to form the dosage forms. During the freeze-drying process, the water is sublimated from the frozen units. In some embodiments, the frozen units can be loaded onto the shelves of a freeze-drier. Once the frozen units are in the freeze-drier, the freeze-drying cycle can be initiated. In some embodiments, a vacuum can be pulled and the shelf temperature raised once the freeze-drying cycle is initiated. The freeze-drier can operate at low pressure (i.e., vacuum).

The freeze-dried dosage forms can be removed from the freeze-drier and inspected for any defects. On completion of the freeze drying cycle, the dosage forms can be sealed (e.g., lidding foil applied to blister). The dosage forms of the present disclosure are dissolving dosage forms and accordingly have the distinct advantage of a faster disintegrating time.

Figure 3:
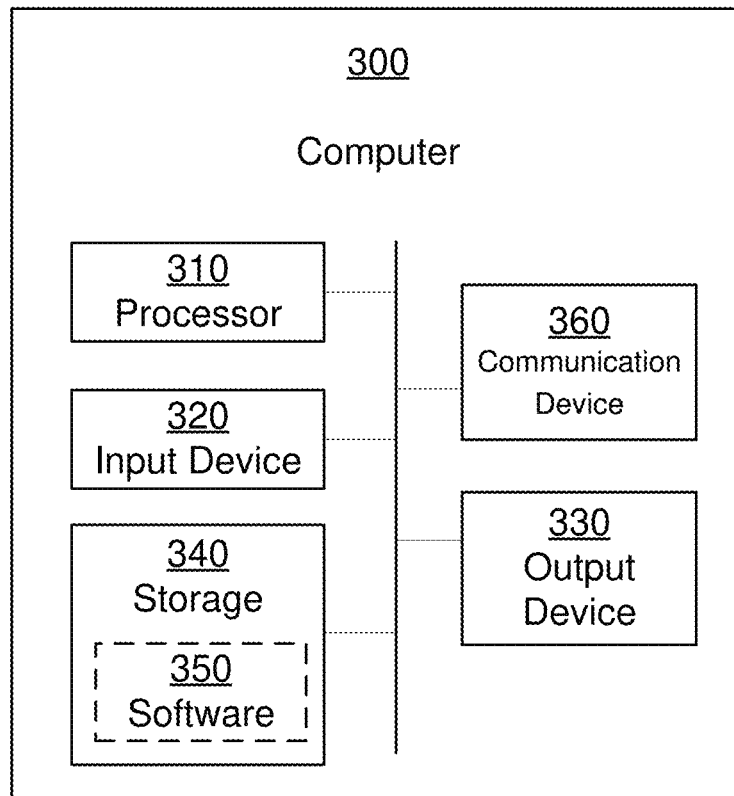
FIG. 3 depicts a computer, in accordance with some embodiments.

FIG. 3 illustrates a computer, in accordance with some embodiments. Computer 300 can be a component of a system for dosing a pharmaceutical formulation, as described above and with respect to FIGS. 1 and 2. In some embodiments, computer 300 may be configured to execute a method for dosing a pharmaceutical formulation, as described above.

Computer 300 can be a host computer connected to a network. Computer 300 can be a client computer or a server. As shown in FIG. 3, computer 300 can be any suitable type of microprocessor-based device, such as a personal computer; workstation; server; or handheld computer device, such as a phone or tablet. The computer can include, for example, one or more of processor 310, input device 320, output device 330, storage 340, and communication device 360.

Input device 320 can be any suitable device that provides input, such as a touch screen or monitor, keyboard, mouse, or voice-recognition device. Output device 330 can be any suitable device that provides output, such as a touch screen, monitor, printer, disk drive, or speaker.

Storage 340 can be any suitable device that provides storage, such as an electrical, magnetic, or optical memory, including a RAM, cache, hard drive, CD-ROM drive, tape drive, or removable storage disk. Communication device 360 can include any suitable device capable of transmitting and receiving signals over a network, such as a network interface chip or card. The components of the computer can be connected in any suitable manner, such as via a physical bus or wirelessly. Storage 340 can be a non-transitory computer-readable storage medium comprising one or more programs, which, when executed by one or more processors, such as processor 310, cause the one or more processors to execute methods described herein, such as all or part of the methods described above with respect to dosing a pharmaceutical formulation.

Software 350, which can be stored in storage 340 and executed by processor 310, can include, for example, the programming that embodies the functionality of the present disclosure (e.g., as embodied in the systems, computers, servers, and/or devices as described above). In some embodiments, software 350 can be implemented and executed on a combination of servers such as application servers and database servers.

Software 350 can also be stored and/or transported within any computer-readable storage medium for use by or in connection with an instruction execution system, apparatus, or device, such as those described above, that can fetch and execute instructions associated with the software from the instruction execution system, apparatus, or device. In the context of this disclosure, a computer-readable storage medium can be any medium, such as storage 340, that can contain or store programming for us by or in connection with an instruction execution system, apparatus, or device.

Software 350 can also be propagated within any transport medium for use by or in connection with an instruction execution system, apparatus, or device, such as those described above, that can fetch and execute instructions associated with the software from the instruction execution system, apparatus, or device. In the context of this disclosure, a transport medium can be any medium that can communicate, propagate, or transport programming for use by or in connection with an instruction execution system, apparatus, or device. The transport-readable medium can include, but is not limited to, an electronic, magnetic, optical, electromagnetic, or infrared wired or wireless propagation medium.

Computer 300 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Computer 300 can implement any operating system suitable for operating on the network. Software 350 can be written in any suitable programming language, such as C, C++, Java, or Python. In various embodiments, application software embodying the functionality of the present disclosure can be deployed in different configurations, such as in a client/server arrangement or through a Web browser as a Web-based application or Web service, for example.

The preceding description sets forth exemplary methods, parameters and the like. It should be recognized, however, that such description is not intended as a limitation on the scope of the present disclosure but is instead provided as a description of exemplary embodiments. The illustrative embodiments described above are not meant to be exhaustive or to limit the disclosure to the precise forms disclosed. Many modifications and variations are possible in view of the above teachings. The embodiments were chosen and described to best explain the principles of the disclosed techniques and their practical applications. Others skilled in the art are thereby enabled to best utilize the techniques, and various embodiments with various modifications as are suited to the particular use contemplated.

Although the disclosure and examples have been thoroughly described with reference to the accompanying figures, it is to be noted that various changes and modifications will become apparent to those skilled in the art. Such changes and modifications are to be understood as being included within the scope of the disclosure and examples as defined by the claims. In the preceding description of the disclosure and embodiments, reference is made to the accompanying drawings, in which are shown, by way of illustration, specific embodiments that can be practiced. It is to be understood that other embodiments and examples can be practiced, and changes can be made without departing from the scope of the present disclosure.

Although the preceding description uses terms first, second, etc. to describe various elements, these elements should not be limited by the terms. These terms are only used to distinguish one element from another.

Also, it is also to be understood that the singular forms "a," "an," and "the" used in the preceding description are intended to include the plural forms as well unless the context indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

The term "if" may be construed to mean "when" or "upon" or "in response to determining" or "in response to detecting," depending on the context.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims.

The invention claimed is:

1. A system for dosing a pharmaceutical formulation comprising:
   a recirculation system comprising a density flow meter configured to measure a density of the pharmaceutical formulation;
   at least one pump fluidly connected to the recirculation system, wherein the at least one pump is configured to displace the pharmaceutical formulation from the recirculation system into preformed molds and is configured to stop displacing the pharmaceutical formulation when the density of the pharmaceutical formulation measured by the density flow meter is below a predetermined threshold.

2. The system of claim 1, further comprising a computer, wherein the computer, the density flow meter, and the at least one pump are communicatively coupled with one another.

3. The system of claim 2, wherein the density flow meter is configured to send data comprising the density of the pharmaceutical formulation to the computer.

4. The system of claim 3, wherein the computer is configured to send one or more instruction or control signals to the at least one pump to alter an activation state of the pump.

5. The system of claim 4, wherein the activation state comprises an on configuration and an off configuration.

6. The system of claim 5, wherein the one or more instruction or control signals sent from the computer to the at least one pump comprises a signal to turn the at least one pump off when the data comprising the density of the pharmaceutical formulation is below a predetermined threshold.

7. The system of claim 2, wherein the computer, the density flow meter, and the at least one pump are wirelessly communicatively coupled with one another.

8. The system of claim 1, wherein the pharmaceutical formulation comprises at least one surfactant.

9. The system of claim 8, wherein the surfactant comprises at least one of sodium lauryl sulfate and sodium docusate.

10. A method for dosing a pharmaceutical formulation, the method comprising:
   measuring a density of the pharmaceutical formulation;
   dosing the pharmaceutical formulation into preformed molds;
   stopping the dosing of the pharmaceutical formulation into preformed molds when the measured density of the pharmaceutical formulation is below a predetermined threshold.

11. The method of claim 10, wherein a density flow meter is configured to send data comprising the density of the pharmaceutical formulation to a computer.

12. The method of claim 11, wherein the computer is configured to send one or more instruction or controls signals to stop the dosing of the pharmaceutical formulation when the data comprising the density of the pharmaceutical formulation is below a predetermined threshold.

13. The method of claim 12, wherein the computer sends the one or more instruction or control signals to stop dosing of the pharmaceutical formulation to at least one pump.

14. The method of claim 10, wherein the pharmaceutical formulation comprises at least one surfactant.

15. The method of claim 14, wherein the surfactant comprises at least one of sodium lauryl sulfate and sodium docusate.

* * * * *